United States Patent
Mueller et al.

(10) Patent No.: US 8,119,550 B2
(45) Date of Patent: Feb. 21, 2012

(54) PROCESS FOR EPOXIDATION AND CATALYST TO BE USED THEREIN

(75) Inventors: Ulrich Mueller, Neustadt (DE); Georg Krug, Moerlenbach (DE); Peter Bassler, Viernheim (DE); Hans-Georg Goebbel, Kallstadt (DE); Peter Rudolf, Ladenburg (DE); Joaquim Henrique Teles, Otterstadt (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 493 days.

(21) Appl. No.: 10/526,939

(22) PCT Filed: Sep. 16, 2003

(86) PCT No.: PCT/EP03/10287
§ 371 (c)(1),
(2), (4) Date: Mar. 8, 2005

(87) PCT Pub. No.: WO2004/026467
PCT Pub. Date: Apr. 1, 2004

(65) Prior Publication Data
US 2006/0167286 A1    Jul. 27, 2006

(51) Int. Cl.
*B01J 29/06* (2006.01)
*C07D 301/19* (2006.01)

(52) U.S. Cl. .......... 502/60; 502/85; 502/214; 423/713; 423/716; 423/326; 549/529

(58) Field of Classification Search .............. 502/214, 502/60, 85; 423/713, 716, 326; 549/529
See application file for complete search history.

(56) References Cited

U.S. PATENT DOCUMENTS

| | | | |
|---|---|---|---|
| 3,257,310 A * | 6/1966 | Plank et al. ............ 208/120.05 |
| 4,410,501 A | 10/1983 | Taramasso et al. |
| 4,605,637 A | 8/1986 | Chang et al. |
| 4,701,428 A | 10/1987 | Bellussi et al. |
| 5,041,652 A | 8/1991 | Padovan et al. |
| 5,412,122 A | 5/1995 | Saxton et al. |
| 5,466,835 A | 11/1995 | Nemeth et al. |
| 5,919,430 A | 7/1999 | Hasenzahl et al. |
| 6,054,112 A * | 4/2000 | Hasenzahl et al. .......... 423/705 |
| 6,106,803 A | 8/2000 | Hasenzahl et al. |
| 6,169,050 B1 | 1/2001 | Catinat et al. |
| 6,281,369 B1 * | 8/2001 | Cooker et al. ............ 549/533 |
| 6,288,004 B1 * | 9/2001 | Balducci et al. ............ 502/85 |
| 2004/0053772 A1 | 3/2004 | Muller et al. |

FOREIGN PATENT DOCUMENTS

| | | |
|---|---|---|
| DE | 102 32 406 | 1/2004 |
| EP | 0 200 260 | 12/1986 |
| EP | 0 311 983 | 4/1989 |
| EP | 0 389 041 | 9/1990 |
| EP | 0 405 978 | 1/1991 |
| WO | 94/02245 | 2/1994 |
| WO | 95/19222 | 7/1995 |
| WO | 98/55228 | 12/1998 |
| WO | 98/55229 | 12/1998 |
| WO | 99/29426 | 6/1999 |
| WO | 99/52626 | 10/1999 |
| WO | 03/042101 | 5/2003 |
| WO | WO 2004/024321 | 3/2004 |

OTHER PUBLICATIONS

Meier, W.M. et al. "Atlas of Zeolite Structure Types", Zeolites, vol. 17, pp. A3-A5 1996.
Trawinski, Helmut et al. "Zentrifugen und Hydrozyklone", Ullmann's Encyclopedia of Industrial Chemistry, 4$^{th}$ edition, vol. 2, pp. 204-224 1972.
European Official Communication issued Sep. 24, 2010 in European Application No. 03797305.4, filed Sep. 16, 2003.
European Office Action mailed Sep. 1, 2009.

* cited by examiner

*Primary Examiner* — Elizabeth Wood
(74) *Attorney, Agent, or Firm* — Oblon, Spivak, McClelland, Maier & Neustadt, L.L.P.

(57) ABSTRACT

The present invention relates to a process for treating a solid material containing at least one zeolite and being at least partly crystalline or treating a shaped body obtained from said solid material wherein said solid material or shaped body is brought in contact with a composition containing water after at least one of the following steps of an integrated process for producing a solid material or a shaped body containing at least one zeolite: (i) after step (II) of separating the at least partly crystalline solid material from its mother liquor or (ii) after step (S) of shaping said solid material into a shaped body or (iii) after a step (C) of calcining said solid material or said shaped body. The present invention furthermore relates to the solid material obtainable by the inventive process and the shaped body obtainable by the inventive process. The present invention also relates to the use of the solid material or the shaped body as mentioned above as a catalyst in chemical reactions, in particular in reactions of compounds containing at least one C-C double bond with at least one hydroperoxide.

17 Claims, 1 Drawing Sheet

PROCESS FOR EPOXIDATION AND CATALYST TO BE USED THEREIN

CROSS-REFERENCE TO RELATED APPLICATIONS

The present application is a 35 U.S.C. § 371 National Stage patent application of International patent application PCT/EP03/010287, filed on Sep. 16, 2003, which claims priority to U.S. patent application 10/244,527, filed on Sep. 17, 2002, which is abandoned.

BACKGROUND OF THE INVENTION

1. Field Of The Invention

The present invention relates to a process for treating a solid material containing at least one zeolite and being at least partly crystalline or treating a shaped body obtained from said solid material wherein said solid material or shaped body is brought in contact with a composition containing water after at least one of the following steps of an integrated process for producing a solid material or a shaped body containing at least one zeolite: (i) after step (II) of separating the at least partly crystalline solid material from its mother liquor or (ii) after step (S) of shaping said solid material into a shaped body or (iii) after a step (C) of calcining said solid material or said shaped body. The present invention furthermore relates to the solid material obtainable by the inventive process and the shaped body obtainable by the inventive process. The present invention finally relates to the use of the solid material or the shaped body as mentioned above as a catalyst in chemical reactions, in particular in reactions of compounds containing at least one C-C double bond with at least one hydroperoxide.

2. Description Of The Background

Integrated processes for the manufacture of solid materials containing a zeolite and said solid materials as such are described in the prior art. Particularly to be mentioned is WO 98/55229. The focus of this reference is on the binding materials used to forming and/or compacting the solid materials containing a zeolite into a shaped body. The WO 98/55229 is silent as to a treatment of the solid material obtained from the synthesis solution with any composition containing water.

Also to be mentioned is DE 102 32 406.9 which relates to an integrated process for manufacturing solid materials containing a zeolite. Said document describes various methods for separating the solid material from its mother liquor, including methods of ultra-filtration and spray-drying. However, said document does not teach the subsequent treatment of the materials so separated from the mother liquor with a composition containing water or such a treatment at any other subsequent stage of the integrated process.

SUMMARY OF THE INVENTION

The object of the present invention was to provide a process for producing a solid material or a shaped body containing at least one zeolite and being at least partially crystalline, wherein said process provides a catalytic material which is improved over the materials of the prior art with respect to at least one catalytic performance characteristic.

DETAILED DESCRIPTION OF THE INVENTION

Figure 1:
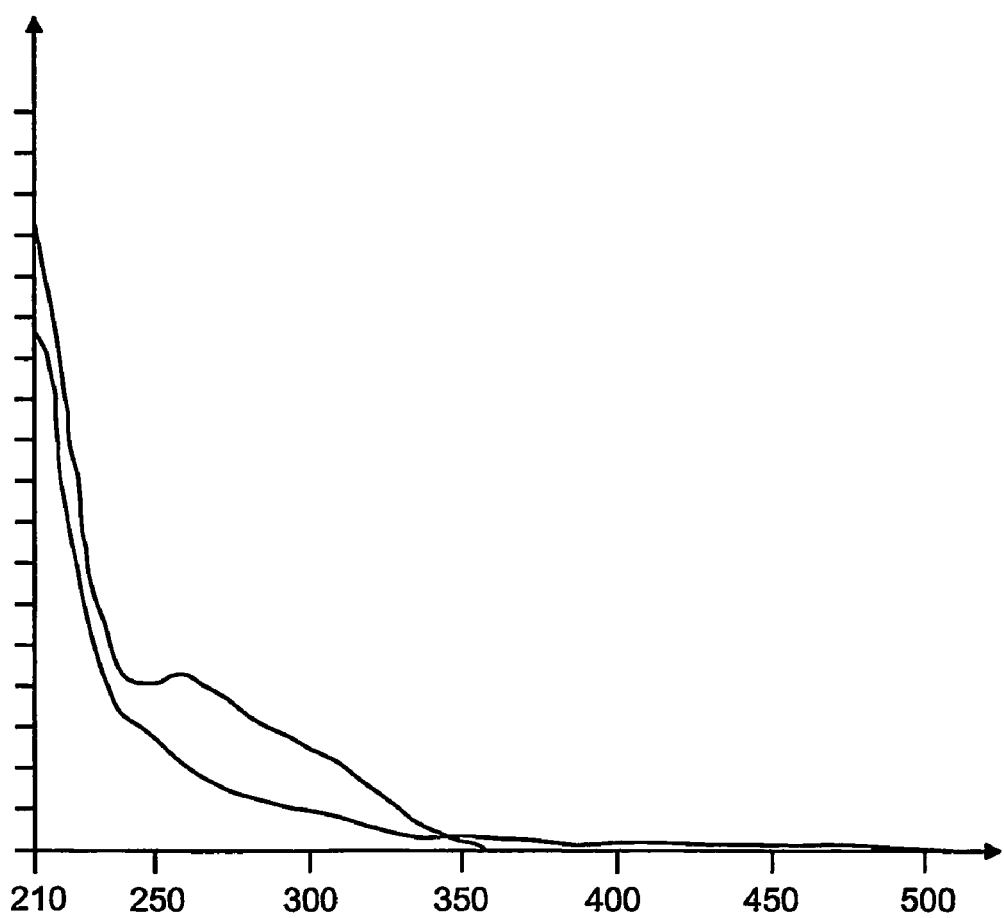
FIG. 1 is a graph showing UV/VIS spectra for a solid material according to the present invention and a solid material not according to the present invention.

Surprisingly, it has been found that the catalytic properties of solid materials containing at least one zeolite can be significantly improved, in particular with respect to their selectivity, if the solid material is subjected to an additional treatment with a composition containing water. The inventive step of treating the solid material containing at least one zeolite with a composition containing water can be performed after at least one of the following two steps of the integrated process for producing a solid material containing at least one zeolite: (i) after step (II) of separating the at least partly crystalline solid material from its mother liquor or (ii) after a step (C) of calcining said solid material.

Similarly, the catalytic properties of a shaped body are improved if the shaped body is subjected to the inventive treatment with a composition containing water after a step (S) of shaping a shaped body from the solid material described above, optionally in conjunction with a step (C) of calcining.

Advantageously, the treatment of the solid material containing at least one zeolite with a composition containing water can be performed in either the reactor that is used for synthesizing the solid material containing at least one zeolite (autoclave) or in the reactor in which the solid material or the shaped body made from said solid material is used as catalyst, i.e. in the reaction container. Therefore, the inventive process does not require an additional (reaction) stage.

The catalytic material (solid material or shaped body) obtainable by the inventive process described above can be used for any catalytic reaction, and preferably in a catalytic reaction in which it improves at least one reaction parameter or catalyst performance characteristic, such as selectivity, yield, activity, over the respective values obtained using catalytic material that has not been subjected to the inventive treatment with a composition containing water.

Preferably, the catalytic material obtainable by the inventive process is used in reactions of compounds containing at least one C-C-double bond with at least one hydroperoxide.

The present invention relates to the above-described process for producing a solid material containing at least one zeolite, to the solid material obtainable by this process, to the shaped body obtainable from the solid material that is produced according to the inventive process, as well as to the use of the solid material and/or the shaped body in chemical reactions, in particular in epoxidation reactions.

In the following, a glossary of the most important expressions used in the context of the present invention is given.

A "synthesis mixture" as used in the context of the present invention pertains to any mixture which yields, by means of crystallization, a mixture containing a solid material that is at least partially crystalline and a fluid material. Preferably, the synthesis mixture contains at least a Si source (Si precursor), a transition metal oxide source (transition metal precursor) and a mineralizing and/or structure forming agent. In particular, reference is made to all synthesis mixtures known to the expert in the field of zeolite preparation, particularly the hydrothermal treatment of gels. The synthesis mixture may be e.g. a sol, gel, solution, or a suspension.

As far as the phases involved in or resulting from the reaction of the synthesis mixture are concerned, after the reaction of the synthesis mixture, it is preferred to obtain a mother liquor containing a solid material in suspension. In the context of the present application, the solid material should be (i) at least partially crystalline and (ii) contain at least one zeolite material.

"Zeolites" as related to in the context of the present invention are crystalline alumosilicates with well-ordered channel or cage structures containing micropores. The expression "micropore" as used in the context of the present invention corresponds to the definition given in "Pure Applied Chemistry", Vol. 45, p. 71 ff., in particular p. 79 (1976). According to this definition, micropores are pores with a pore diameter of less than 2 μm. The network of these zeolites is made of $SiO_4$ and $AlO_4$-tetrahedra that are bridged via shared oxygen bonds. An overview of the known structures can be found in, e.g., W. M. Meier und D. H. Olson in "Atlas of Zeolite Structure Types", Elsevier, $4^{th}$ Ed., London 1996. In addition to micropores, solid materials or shaped bodies according to the invention may contain mesopores and/or macropores as well.

"Solid materials" as obtained, for example, after the crystallization of the synthesis mixture, are to be understood in the context of the present invention as any known material which displays at least the following properties: (i) it contains at least one zeolite material and (ii) is different from the synthesis mixture described above in the sense that a separation of said solid material from its mother liquor is possible and/or concentrating of the solid material by, e.g., ultra-filtration is possible. Typically, the solid material prevails as particles suspended in the mother liquor.

A "mother liquor" in the context of the present invention is any liquid phase that may contain an unlimited number of substances dissolved therein, however in itself is not a solid material. In particular, the mother liquor may contain adjuvants dissolved therein. In the context of the present invention, a mother liquor can only occur after step (I) of the integrated process as described above. Typically, a mother liquor is the liquid phase in which the solid material is suspended in the form of particles. Said mixture (I) is then subjected to step (II) of separating and/or concentrating of the solid material in mixture (I).

Step (II) of the present invention relates to concentrating and/or separating of the solid material in the mother liquor and/or from the mother liquor, wherein the mixture (I) containing the solid material is obtained from step (I). The term "concentrating and/or separating" is to be understood in the context of the present invention as any step that at least results in that, at the end of step (II), the solid material content in the mixture is increased and/or the solid material is separated partly or entirely from the mother liquor.

The complete "separation" of the solid material from the mixture (the suspension) is explicitly contained in the definition of "concentrating" as a specific case. Such methods of separating and/or concentrating include, but are not limited to, spray-drying or ultra-filtration and will be described in more detail below. The terms "filtration", "ultra-filtration", and "spray-drying" as well as other methods of concentrating and/or separating the solid material from the mother liquor are described in detail in DE 102 32 406.9, the respective content of which is hereby incorporated by reference.

A "shaped body" as used in the context of the present invention is to be understood to be any three dimensional entity, which can be obtained by any of the shaping steps (S) mentioned below. The shaped body is obtained in a typical manner by means of compacting of the solid material described above. Said solid material may originate from steps (II) and/or (III), using optional steps of calcining (C).

The expressions "granulating" and "agglomerating" as used in the context of the present invention are to be seen as synonymous and describe, respectively, any conceivable process that can be used to increase the diameter of the particles obtained from step (II). Said increase of the particle diameter can be achieved by baking the particles together or by growing on the particles layer by layer. The process of granulating thereby includes, but is not limited to, processes taking advantage of the phenomenon of wetting of the particles by at least one liquid. Furthermore, binding materials may be added to the mixture in order to enhance or enable the agglomerating and/or granulating of the particles.

A "binding material" as used in the context of the present invention is to be understood to be any material that enables a physical, chemical, or physical-chemical bond between the substances constituting the particle. Such binding materials may be used in the step (S) of shaping or forming the solid material into a shaped body as well. Reference is made to the description of binding materials in that context.

The inventive treatment of a solid material or a shaped body produced therefrom, both containing at least one zeolite and being at least partially crystalline, with a composition containing water is preferably part of an integrated process, namely an integrated process producing a mechanically stable solid material or a shaped body containing at least one zeolite material. Schematically, such an integrated process can be characterized by the following steps:

(I) at least partial crystallization of at least one solid material containing at least one zeolite out of a synthesis mixture, resulting in mixture (I) containing at least said solid material and a mother liquor;

(II) separating and/or concentrating of the solid material from mixture (I);

(W) bringing the solid material from step (II) in contact with a composition containing water;

(III) agglomerating or granulating or agglomerating and granulating of the solid material from step (W);

wherein step (III) is optional. Step (II) may additionally include the drying and/or washing of the solid material, possibly also in several iterations.

In a preferred embodiment, step (II) is repeated after step (W).

Additionally, and/or optionally the following steps may be part of the integrated process as well:

(S) shaping of the solid material into shaped bodies subsequent to steps (W) or (III);

(C) Calcining of the solid material and/or the shaped body at temperatures higher than 400° C.;

wherein the step (C) of calcining may be performed at least once after at least one of the following steps of the integrated process: (II), (W), or (III).

In a preferred embodiment, step (W) is performed after step (S) of shaping the solid material, wherein said step (W) either replaces the step (W) performed after step (II), as described in the embodiment above, or is performed in addition to a step (W) performed after step (II).

In the present application, the inventive solid material containing at least one zeolite material or the shaped body obtainable therefrom is discussed in the context of applications in the field of catalysis. This, however, cannot be construed as a limitation of the use of the solid material and/or the shaped body to the field of catalysis. The explicit discussion of examples in the field of catalysis is illustrative only. The inventive material may be used in other fields as well.

In the following, the individual steps of the integrated process for producing a solid material and/or shaped body are summarized, wherein the solid material and/or the shaped body contain(s) at least one zeolite material and is/are at least partially crystalline. Of particular importance is the step (W) representing the inventive step.

Step I: (Partial) Crystallization of the Synthesis Mixture

As far as the least one zeolite material present in the inventive solid material and/or the inventive shaped body is concerned, no limitations exist. Preferably, a zeolite containing titanium, zirconium, chromium, niobium, iron, bor, vanadium is employed. Particularly preferably, a zeolite containing titanium is employed, wherein zeolites known to the expert in the field as "titanium silicalites" (TS) are particularly preferred.

Such zeolites containing titanium, in particular those displaying a crystalline structure of the MFI-type as well as ways for producing them are described, for example, in WO 98/55228, WO 98/55229, WO 99/29426, WO 99/52626, EP-A 0 311 983, or EP-A 405 978. The respective content of these documents is hereby incorporated by reference. In addition to Si and Ti, said zeolite materials may contain additional elements, such as aluminum, zirconium, tin, iron, cobalt, nickel, gallium, bor, or small amounts of fluorine. It is possible that the titanium of the zeolite is partly or completely replaced by vanadium, zirconium, or niobium, or any mixture of two or more of these components.

Zeolites containing titanium and displaying a MFI-structure are known to yield a characteristic pattern in x-ray diffraction. Furthermore, these materials display a vibration band in the infrared (IR) at approximately 960 cm$^{-1}$. Therefore, it is possible to distinguish the zeolites containing titanium from crystalline or amorphous $TiO_2$-phases or from alkali metal titanates.

Typically, said zeolites containing titanium, zirconium, niobium, iron, and/or vanadium are produced by starting with a synthesis mixture, i.e. an aqueous solution of a $SiO_2$-source, a source for titanium, zirconium, chromium, niobium, iron, and/or vanadium, such as titanium oxide, titanium dioxide, or the respective metal oxide, as well as an organic base containing nitrogen to be used as a template. The term "template", in this context refers to materials that can be used as a mineralizing agent or as a structuring agent or both.

If necessary, or advantageous, additional compounds may be added. The reaction of the synthesis mixture is performed in a pressure-tight container (autoclave) at elevated temperatures over the course of several hours or days. Thereby, a product that is at least partly crystalline is obtained. In the context of the present invention, this step of producing a solid material containing zeolite and being at least partly crystalline, is referred to as step (I).

In the context of step (I), in a preferred embodiment, at least one template substance is used that yields a specific and desired pore size. In principle there are no restriction with respect to the at least one template substance, apart from the fact that said template substances have to contribute, at least partly, to pore formation. Suited template compounds may be quaternary ammonium salts such as tetrapropylammonium hydroxide, tetrapropylammoniumbromide, tetraethylammoniumhydroxide, tetraethylammonium bromide or diamine or other template substances known from the literature.

In a further preferred embodiment, the at least one zeolite material is selected from the following group: zeolites containing at least one of the following elements: titanium, germanium, tellurium, vanadium, chromium, niobium, zirconium, particularly those having a pentasil zeolite structure, in particular the structural types that can be, via x-ray diffraction, assigned to the structure types of ABW-, ACO-, AEI-, AEL-, AEN-, AET-, AFG-, AFI-, AFN-, AFO-, AFR-, AFS-, AFT-, AFX-, AFY-, AHT-, ANA-, APC-, APD-, AST-, ATN-, ATO-, ATS-, ATT-, ATV-, AWO-, AWW-, BEA-, BIK-, BOG-, BPH-, BRE-, CAN-, CAS-, CFI-, CGF-, CGS-, CHA-, CHI-, CLO-, CON-, CZP-, DAC-, DDR-, DFO-, DFT-, DOH-, DON-, EAB-, EDI-, EMT-, EPI-, ERI-, ESV-, EUO-, FAU-, FER-, GIS-, GME-, GOO-, HEU-, IFR-, ISV-, ITE-, JBW-, KFI-, LAU-, LEV-, LIO-, LOS-, LOV-, LTA-, LTL-, LTN-, MAZ-, MEI-, MEL-, MEP-, MER-, MFI-, MFS-, MON-, MOR-, MSO-, MTF-, MTN-, MTT-, MTW-, MWW-, NAT-, NES-, NON-, OFF-, OSI-, PAR-, PAU-, PHI-, RHO-, RON-, RSN-, RTE-, RTH-, RUT-, SAO-, SAT-, SBE-, SBS-, SBT-, SFF-, SGT-, SOD-, STF-, STI-, STT-, TER-, THO-, TON-, TSC-, VET-, VFI-, VNI-, VSV-, WIE-, WEN-, YUG-, ZON, as well as mixed structures of at least two or more of the aforementioned structures. Furthermore, it is conceivable to use zeolites containing titanium with the structure of ITQ-4, IrQ-9, SSZ-24, TTM-1, UTD-1, CIT-1 or CIT-5. Further zeolites containing titanium are such of the structure types ZSM-48 or ZSM-12.

Zeolites containing titanium of the structure MFI, MEL or MFI/MEL mixed structures, as well as MWW, BEA or mixed structures thereof are preferred in the context of the present invention. Further preferred in the context of the present invention are these zeolite catalysts containing titanium that are referred to, in general, as "TS-1", "TS-2" or "TS-3", as well as zeolites containing titanium displaying a structure that is isomorphous to β-zeolite.

Step (II): Separating and/or Concentrating

In step (II) the solid material is separated from the mother liquor and/or is concentrated in the mother liquor. Step (II) is performed with mixture (I) from step (I). Methods of separating and/or concentrating include but are not limited to filtration, ultrafiltration, diafiltration, centrifuge methods, spray drying, spray granulating, etc.

This step (II) of concentrating and/or separating is preferably performed prior to the inventive step (W) of bringing the solid material in contact with a composition containing water and after the step (I) of crystallizing the solid material. The purpose of step (II) is to increase the solid content in the mixture resulting from step (I). For details of filtration and/or concentration, reference is made to DE 102 32 406.9, the respective content of which is hereby incorporated by reference.

Preferably, the solid material is concentrated first and then separated from the mother liquor by filtration. For example, the method of ultrafiltration may be used for concentrating the solid material in the retentate, while the solid material may be separated from all or parts of the mother liquor by means of conventional filtration. With respect to conventional filtration, all methods known to the expert in the art may be used such as cake filtration or methods involving a centrifuge.

In a preferred embodiment, step (II) consists of bringing an inert support body in contact with the synthesis mixture from step (I). As far as the "inert support body" is concerned, no limitations exist, as long as the inert support body does not react noticeably with the synthesis mixture or any component thereof and said inert support body is capable of accommodating, at least partly, the solid material contained in the synthesis mixture from step (I), preferably in the form of a (thin) film. Such inert support bodies may include but are not limited to beads or pellets made form technical ceramic materials such as alumosilicate ceramics, alkali alumosilicate ceramics, aluminum oxide based ceramics (e.g. mullit), magnesium silicates (e.g. steatit, cordierit). The use of steatit or mullit is preferred. Said inert support bodies may be porous or dense, wherein the use of dense support bodies is preferred.

Said support bodies may be brought in contact with the synthesis mixture from step (I) by means of all methods known to expert in the context of bringing a solid body in contact with a fluid medium. Spraying of the synthesis mixture onto the support bodies, dipping the support bodies into the synthesis mixture or saturating/soaking of the inert support bodies in the synthesis mixture are preferred. In case the method of bringing in contact is soaking/dipping/saturating, in a preferred embodiment, the soaked/dipped/saturated support bodies are exposed to an atmosphere with a partial pressure of the liquid medium of the synthesis mixture (e.g. water) lower than the pressure of the pure liquid, so that the liquid medium may, at least partly, evaporate.

As a result of said step of bringing inert support bodies in contact with the synthesis mixture from step (I), a (thin) film containing the solid material containing at least one zeolite and being at least partly crystalline forms on the support body and/or in the pores, if the support body is porous. The thickness of the film so formed may range from 1 μm to 1500 μm. In a preferred embodiment, the thickness of the film ranges from 5 μm to 50 μm. The result of this embodiment is referred to a "solid material" in the context of the present invention and is processed the same way as the solid material obtained by spray drying or ultrafiltration.

The solid material obtained after step (II) may be optionally subjected to at least one step of washing and to at least one step of drying of the solid material. Furthermore, after the at least one step of drying, the solid material may also be calcined at temperatures of 400° C. and higher (see description of the step (C) of calcining given below).

Step (W): Treatment of the Solid Material with a Composition Containing Water

Subsequent to step (II) of concentrating and/or separating, the solid material may be subjected to the inventive treatment of bringing the solid material in contact with a composition containing water.

As far as the term "bringing in contact" is concerned, any method is conceivable, in which the solid material is brought in physical contact with a composition containing water. This includes, but is not limited to forming a slurry, suspension or mixture of the solid material in or with the composition containing water, the composition being preferably in a liquid phase, spraying the solid material with the composition containing water, subjecting the solid material to the composition containing water in the form of vapor and/or steam. It is particularly preferred to form a slurry of the solid material with the composition containing water in a stirring tank.

Preferably, the same stirring tank is used for step (W) that has already been used for crystallizing the solid material out of the synthesis mixture. For additional physical contact between the solid phase and the composition containing water, any means for stirring or otherwise mechanically acting the mixture containing the solid material and the composition containing water known to the expert in this field can be employed. Other methods of mixing and/or agitating, such as ultrasound agitation, magnetic stirring and the like are conceivable as well. Preferably the slurry of the solid material is brought in contact with a composition containing water in a tank vessel with a mechanical stirring device.

As far a the composition containing water is concerned, any substance can be used that contains, at least in parts, water in any of its modifications. These modifications include the liquid phase, the solid phase, vapor, steam, super critical water. Furthermore, the water may by mixed with other substances. Preferably water is used as such in the liquid phase or as steam. If water is used in the liquid phase, deionized water is preferred. Any method to deionize water known to the expert in the art is included, such as distillation or removing of electrolytes over an ion exchanger. While not preferred, the use of water containing salt and/or of water that is acidic or basic is conceivable as well.

For specific applications, bringing the solid material in contact with an aqueous ammonia solution may be preferred. In this case, a solution of ammonia in water is preferred, wherein the content of ammonia in water, given in % by weight with respect to the total weight, ranges from 5 to 60, preferably from 10 to 30. If a composition containing water and ammonia is used, step (W) is preferably performed at pressures elevated with respect to ambient pressure and not exceeding several hundred bars.

As far as the ratio between the amount of solid material and the composition containing water is concerned, no principal limitations exist, save for the fact that the mixture or slurry should have viscous or hydraulic properties conducive to mechanical stirring.

Furthermore, it is preferred that the treatment of bringing the solid material in contact with a composition containing water is performed at a temperature elevated with respect to room temperature. Temperatures between room temperature and 750° C. are preferred. Temperatures between 100° C. and 250° C. are particularly preferred, while temperatures between 120° C. and 175° C. are further preferred.

As far as the duration of the inventive treatment is concerned, no limitations exist, as long as the treatment results in an improved performance of the catalyst over a catalyst that had not been subjected to that treatment. As a measure for the increased performance, improved activity, selectivity and/or yield may be used. Increased mechanical stability or improved properties that are otherwise relevant for the process of interest can be used as well. In a preferred embodiment, the inventive treatment is performed for the duration of 12 to 24 hours.

The inventive treatment (W) of the solid material with a composition containing water can be performed with any type of solid material. The solid material may be the material obtained from step (II) without drying or calcining. However, it is preferred that the solid material from step (II) has been dried and/or calcined before the inventive treatment. It is further preferred, that the solid material has been washed, dried and optionally calcined prior to step (W). It is further preferred that the solid material has been obtained by spray granulation and/or ultrafiltration (in conjunction with conventional filtering).

In a preferred embodiment, performing step (W) after step (II) is optional if, but only if, the step (W) is performed at a later stage of the integrated process, for example after step (S) as described below or after step (S) in conjunction with step (C). In summary, step (W) has to be performed at least once during the integrated process for producing a solid material or a shaped body containing at least one zeolite.

After step (W) has been performed, i.e. after the solid material has been brought into contact with the composition containing water, the composition containing water may be removed from the solid material and/or the solid material may be concentrated in the composition containing water. To achieve this end, step (II) may be repeated. This is, the mixture containing the solid material and composition containing water may be subjected to, e.g., spray drying, ultrafiltration, or ultrafiltration in conjunction with conventional filtration. It may be only subjected to conventional filtration as well.

Step (III): Agglomerating/Granulating

Subsequent to step (W), the solid particles can be increased in their size using any method of agglomerating and/or granulating known to the expert in the field. For a list of methods used in this context, reference is made to DE 102 32 406.9, the respective content of which is hereby incorporated by reference.

Post-treatment

In order to improve the catalytic performance of the find product, subsequent to step (W) or to step (III) or subsequent to both, it is optionally possible to perform at least one step of post-treatment of the material, including but not limited to the following steps: drying, washing, calcining, treating the solid material with a hydrogen peroxide solution. Any combination of these steps is conceivable as well. It is also possible to treat this solid material containing at least one zeolite material with compounds containing alkaline metal, in order to transform the zeolitic material from the H-form into the cationic form. The solid material obtained after step (W) or after step (III) or after any of the two steps in conjunction with any of the steps of post treatment mentioned here, can then be processed further to a shaped body, as described below.

Step (S): Shaping of the Solid Material

The starting point for the process to produce a shaped body containing at least one zeolite is either the solid material after step (II) or the solid material after step (W) or the solid material after step (III), optionally involving any of the steps of post-treatment mentioned in the proceeding paragraph. As it has been mentioned above, if the process so far has involved at least one step (W) of bringing the solid material in contact with a composition containing water, the material obtained after step (S) does not need to be subjected to an inventive step (W). However, if the solid material so far has not been subjected to the inventive treatment (W), the inventive step of bringing the shaped body in contact with at least one composition containing water has to be performed after the step (S) of shaping the solid material or after said step (S) in conjunction with a step (C).

In any case, the step (S) of shaping the solid material involves at least one step of forming a three dimensional material that contains at least one zeolite. As far as this specific (at least one) step of shaping the solid materials is concerned, reference is made to WO 98/55229 and to DE 102 32 406.9 whose respective content is incorporated into the present application by reference.

Preferably, a binding material is added to the solid material resulting from any of the steps mentioned above. Further adjuvants that may be added to the solid material prior to the step (S) include but are not limited to mixtures containing at least one alcohol and water, if suitable one or more organic substances increasing the viscosity, and further substances known from the prior art.

Preferably, the solid material is milled and mixed with silica sol, a dispersion of polystyrene, cellulose and polyethlylene oxide (PEO), as well as with water. Said mixture is homogenized in any type of kneading apparatus. In lieu of kneading, any method of bringing the substances into physical contact may be used. Preferably, the mass obtained by this method shows plastic flow. The shaped body can then be obtained from this mass, e.g., by means of molding, in particular extrusion molding, or by any other method of extrusion known to the expert in the field.

As far as the binding materials are concerned, in principle, every substance can be used that achieves cohesion between the particles that is increased over the cohesion achieved without the presence of the binding material. Preferred binding materials are selected from the group consisting of hydrated silica gel, silicic acid, tetraalkoxy silicates, tetraalkoxy titanates, tetraalkoxy zirconates or mixtures of two or more of the afore-mentioned substances. Tetraalkoxy silicates such as tetramethoxy silicates, tetraethoxy silicates, tetrapropoxy silicates or tetrabutoxy silicates are preferred. Tetramethoxy silicates or tetraethoxy silicates and silica sols are particularly preferred.

Further preferred binding materials are amphiphilic substances, i.e. molecules with a polar and a non-polar part. The use of graphite is conceivable as well. As far as further binding materials are concerned, reference is made to WO 98/55229 and to DE 102 32 406.9 whose respective content is incorporated into the present application by reference.

Said binding materials can be used either alone or as mixtures of two or more thereof, or can be used together with other materials to be used for enabling or enhancing the binding of materials containing at least one zeolite, such as oxides of silicon, bor, phosphor, zirconium, and/or titanium. By way of example, clays are also to be mentioned.

In the process of shaping the solid material into a shaped body, up to approximately 80% by weight of binding materials with respect to the total mass of the shaped body may be used. It is preferred to use from approximately 10 to approximately 75% by weight of binding materials, while using 25% to approximately 45% is particularly preferred.

In the context of the process to produce a shaped body, polymers may be added to create pores of a certain size, a certain volume or a certain size distribution. In the context of the present invention, polymers are preferred that can be dispersed, emulsified or suspended in aqueous solvents. Said at least one polymer is preferably selected from the group of polymer vinyl compounds, such as polystyrene, polyacrylates, polymethacrylates, polyolefins, polyamids, or polyesters. These polymers are removed from the shaped body after the process of forming and/or shaping by means of calcining the shaped body. If polymers are added, the content of polymer during the production of the shaped body amounts to from approx. 5 to approx. 90% by weight, preferably from approx. 15 to approx. 75% by weight, wherein a content ranging from 25 to 55% by weight is particularly preferred. The amounts given in weight-% refer to the amount of polymer in the solid material containing zeolite, respectively.

Furthermore, it is preferred to add a pasting agent. As far as the pasting agent is concerned, any substance known from the prior art to improve the mixing, kneading, or flow properties of the mass can be used. Preferably, organic hydrophilic polymers are used, such as cellulose, starch, polyacrylates, polymethacrylates, polyvinylalcohol, polyvinyl pyrrolidone, polyisobutene, polytetrahydrofuran. Primarily, these substances enable or improve the formation of a plastic mass during the process of kneading, forming, and/or drying by means of bridging the primary particles. Moreover, these adjuvants enable or enhance the mechanical stability of the shaped body during the steps of forming or drying.

These substances are removed from the shaped body by means of calcining after the step of shaping. Further adjuvants are described in EP-A 0 389 041, EP-A 0 200 260, and in WO 95/19222, the respective contents of which are hereby incorporated by reference.

In a preferred embodiment, after having added the binding material to the solid material containing at least one zeolite, the organic substance increasing viscosity is added and the mass is homogenized for 10 to 180 minutes in the kneading apparatus or in the extruder. The temperature applied to the mass is typically about 10° C. under the boiling point of the pasting agent. The pressure is either ambient pressure or is slight over-pressure. In principle, the order of adding additional components to the solid material and the binder is not believed to be critical. The mass obtained as described above is kneaded until a plastic mass can be extruded.

In the context of the present invention, those methods for forming a shaped body from a solid material are preferred, in which the forming can be performed in commercially available extruders. Preferably, extrudates of a diameter ranging from approx. 1 to approx. 10 mm are used, particularly preferred are extrudates with diameters ranging from approx. 2 to approx. 5 mm. Extruders that can be used in the context of the steps described here are described, for example, in "Ullmann's Enzyklopädie der Technischen Chemie", 4$^{th}$ Edition, Vol. 2, p. 205 ff. (1972).

In principle, all methods of shaping and of forming that are known to the expert in the art can be used. Next to extrusion, other known methods are briquetting, pelleting, pressing, sintering, or roasting.

The technique of co-extruding can be employed as well. Here, two materials are co-extruded simultaneously. Preferably the aforedescribed active material (solid material according to the invention) is extruded together with an inert material, i.e. a material that does not react noticeably with the active material. Preferably, the matrix of the extruder is designed so that the active material is extruded as a layer on the inert material. Therefore, strands result whose core is made of the inert material and whose outer layer is the active solid material. In a preferred embodiment, the thickness of the active layer ranges from 1 to 1500 μm, preferably from 5 to 50 μm.

The use of binding materials or other adjuvants is in any event optional. The materials to be compacted may be dry or moist or may prevail as a slurry.

The step of shaping and/or forming can be performed at ambient pressure or at a pressure that is elevated with respect to ambient pressure, for example, in a pressure range from 1 bar to 700 bar. Furthermore, the shaping and/or forming can be performed at ambient temperature or at a temperature increased with respect to ambient temperature, e.g., a temperature in the range of from 20° C. to approx. 300° C. If drying and/or sintering is part of the shaping and/or forming step, temperatures of up to 1500° C. are conceivable. Furthermore, the step of compacting and of forming can be performed at ambient atmosphere or in a controlled atmosphere. Controlled atmospheres include but are not limited to inert gas atmospheres, reducing atmospheres, or oxidizing atmospheres.

Post-treatment of the Shaped Body

After forming and/or shaping (S) the shaped bodies, they are typically dried at temperatures ranging from approx. 30° C. to approx. 140° C. for a time interval typically rangings from 1 h to 20 h. Subsequent to this step, the shaped body is calcined at temperatures ranging from approx. 400° C. to approx. 800° C. and for a time interval ranging from approx. 3 h to approx. 10 h. Calcining can be performed at ambient pressure, preferably in air or in a mixture containing air or under inert conditions.

In another step of post-treatment, the extrudates obtained as described above may be milled and/or crushed. The milling and/or crushing preferably leads to a granulate with an average particle diameter ranging from 0.1 to approx. 5 mm. Particle diameters ranging from approx. 0.5 to 2 mm are particularly preferred.

Subsequent to the step (S) or subsequent to said step (S) in conjunction with any step of post-treatments such as (in particular) drying and calcining, the inventive treatment of bringing the solid material, in this case a shaped body, in contact with a material containing water, i.e., the step (W) may be performed. If the step (W) has not been performed at any point during the integrated process as described above, the implementation of the step (W) at this point is mandatory. If said step (W) has been performed before at least once, the implementation of said step is optional.

If the step (W) is performed at this point, i.e. after the step (S) or the steps (S) and (C) in conjunction, everything that has been disclosed before about the specific embodiments of said step of (W) is valid here as well. In a preferred embodiment, however, the shaped body is charged into the reactor that is used for the desired reaction, typically an epoxidation reaction, and said shaped body is subjected to the treatment with the composition containing water, in the reactor. Preferably the treatment consists in exposing and/or bringing in contact the shaped body with water steam.

In addition to the process for producing a solid material and/or a shaped body as described above, the present invention also relates to the respective material as such.

First of all, the invention relates to a solid material obtainable by a process of treating a solid material containing at least one zeolite and being at least partly crystalline, wherein said solid material is brought in contact with a composition containing water after at least one of the following steps of an integrated process for producing said solid material: (i) after step (II) of concentrating or separating the at least partly crystalline solid material from its mother liquor via, example given, filtration or spray drying, or (ii) after the same step with the additional optional step of drying and/or calcining (C) of the solid material.

In particular, the solid material is obtainable by a sequence of the following steps (I) at least partial crystallization of at least one solid material containing at least one zeolite out of a synthesis mixture, resulting in mixture (I) containing at least said solid material and a mother liquor;
(II) separating and/or concentrating of the solid material from mixture (I);
(W) bringing the solid material from step (II) in contact with a composition containing water;
(III) agglomerating or granulating or agglomerating and granulating of the solid material from step (W);

wherein step (III) is optional. Step (II) may additionally include the drying and/or washing of the solid material, possibly also in several iterations. In a preferred embodiment, step (II) is repeated after step (W).

Said inventive solid material is further characterized by its particular UV/VIS spectra. These spectra clearly indicate, that the material obtained by the inventive process is different from the material that is obtained without using the inventive treatment of bringing the solid material in contact with a composition containing water. This is illustrated in FIG. 1.

Overall, the inventive solid material is characterized by an additional hump, i.e. an increase in the UV/VIS absorbance in the range between approximately 200 and approximately 350 nm, particularly in the range from 250 to 350 nm.

Furthermore, the present invention relates to a shaped body obtained from the solid material described above. The shaped body is obtained by subjecting the solid material to a step (S) of shaping, as described in detail above, and (optionally) to a step (C) of calcining.

If the solid material as described above has been subjected to the inventive treatment (W), the shaped body obtained from that solid material does not have to be subjected to the inventive treatment (W). However, if the solid material has not been subjected to the inventive step (W), the shaped body as obtained by any of the steps (S) mentioned above, has to be subjected to a inventive step (W), consisting in this case of bringing the shaped body in contact with a composition containing water.

Finally the present invention relates to the use of the inventive materials, i.e. the solid material and/or the shaped bodies as catalysts. The materials obtainable by the inventive process or the materials obtained by the inventive process are particularly suited for catalytic reactions involving compounds with at least one C-C-double bond. Particularly preferred is the reaction of at least one compound containing at least one C-C-double bond with at least one hydrogen peroxide. These reactions are also referred to as epoxidation reactions. As far as further possible reactions are concerned for which said catalysts may be employed, reference is made to DE 102 32

406.9 the respective content of which (in particular pages 27 and 28) is hereby incorporated by reference.

FIG. 1 shows on the horizontal axis, i.e. the x-axis, the UV/VIS wavelength given in nm and it shows on the vertical axis, i.e. the y axis, the absorbance in Kubelka-Munk representation. Starting from the left, the lower curve represents the data taken with a solid material obtained by the conventional process, i.e. without subjecting the solid material to the inventive step (W).

By contrast, starting from the left, the upper line shows the respective data obtained from a solid material that has been subjected to the inventive step (W), but otherwise has been prepared the same way as the (non-inventive) material represented by the lower curve. It can be clearly seen that between approximately 200 nm and approximately 350 nm a pronounced hump in the UV/VIS absorbance appears. This pronounced hump is not observed for a solid material that has not been subjected to the inventive step (W).

EXAMPLES

Example 1

Inventive Treatment (W) of a Solid Material 100 g of a calcined titanium zeolite spray granulate (content with respect to titanium 1.5% by weight) were charged into a steel autoclave that can be stirred. The titanium zeolite granulate was stirred together with 1080 g of deionized water at 300 rpm. The duration of the treatment was 24 hours and the temperature was 175° C. After the treatment had been finished, the content of the autoclave was filtered over a nutsch filter and was rinsed three times with a total amount of 1500 ml of deionized water.

The filter cake was dried for 4 hours at 120° C. under air atmosphere. Finally, the mass was calcined for three hours at 550° C. The final yield was 90 g and the material displayed a content in titanium of 1.5 weight %.

Example 2

Shaping of the Inventive Material from Example 1

60 g of the inventive solid material as described in Example 1 were milled and mixed with the following substances: 56.5 g of silica sol (Ludox AS 40% by weight $SiO_2$), a total amount of 32.9 g of a polystyrene dispersion (43.5 weight % of polymer), 2.7 g of methyl cellulose (Walocel) and 0.88 g of polyethylene oxide (PEO). 20 g of water were added to the mass. Said mass was homogenized in a kneading apparatus.

However, the materials were not added at the same time. Specifically, during the process of kneading, the polystyrene dispersion was added within 5 minutes, and after 10 minutes the silica sol was added slowly. After 10 further minutes of kneading, the PEO was added and gobbled for a further 10 minutes. Subsequently, water was added in portions of 5 ml, respectively.

The paste so obtained w<s formed after a total of 60 minutes of kneading and at a extrusion pressure of 70 bars via a extruder having a matrix of 1.5 mm holes. This way the solid material was alternately formed into strands.

The shaped body contained this way was dried for 4 hours at 120° C. (heating ramp of 2 K per minute). Finally, the shaped body was calcined at 490° C. for 4 hours (heating ramp 1 K per minute). The atmosphere was air. The yield was 65.24 g. The content in titainium of the shaped body produced this way was 1.1% by weight. The pore volume as obtained by mercury porosimetry (DIN 66133) was 0.84 ml/g.

Example 3

Oxidation using the Inventive Shaped Body 13.5 g of the catalyst described in Example 2 were loaded into a tube reactor (1.3 m length). The catalyst was exposed at a pressure of about 20 bars to a feed of 48 g/hour of methanol, 8.2 g/hour of hydrogen peroxide (40% by weight) and 4.7 g/hour of propylene (96% by volume of propylene). Temperatures were regulated between 20 and 40° C.

The analysis of the product mixture emerging from the reactor resulted in that after 96 hours, the selectivity for propylene oxide (with respect to $H_2O_2$) was 96.4%. After 416 hours a selectivity of 96% was measured. The formation of oxygen (selectivity with respect to $H_2O_2$) was measured to be 0.6% after 96 hours and 0.6% even after 416 hours.

Comparative Example

Using a catalyst that has not been subjected to the inventive treatment (W) given in Example 1, the following values have been obtained for the selectivity (under otherwise equal conditions): after 90 hours the selectivity of propylene oxide (with respect to $H_2O_2$) was 96.5%. After 427 hours a selectivity of only 91.3% was measured. The formation of oxygen (selectivity with respect to $H_2O_2$) was measured to be 0.6% after 90 hours but already 1.3% after 427 hours.

We claim:

1. An integrated process for treating a solid material comprising at least one zeolite which comprises Ti and being at least partly crystalline, or a shaped body, obtained from said solid material by shaping said solid material into a shaped body, said process comprising:
    bringing said solid material or said shaped body in contact with deionized water at a temperature between 120° C. and 175° C. for a duration of 12 to 24 hours after
    at least partial crystallization of the solid material containing the at least one zeolite out of a synthesis mixture, resulting in mixture (I) containing the solid material and its mother liquor; separating the solid material from its mother liquor wherein said separating is a step (II), and calcining the solid material at temperatures higher than 400° C. wherein said calcining is a step (C); or after
    at least partial crystallization of the solid material containing the at least one zeolite out of a synthesis mixture, resulting in mixture (I) containing the solid material and its mother liquor; separating the solid material from its mother liquor wherein said separating is a step (II), calcining the solid material at temperatures higher than 400° C. wherein said calcining is a step (C), shaping the solid material into the shaped body, wherein said shaping is a step (S), and optionally calcining the shaped body wherein said calcining is a step (C).

2. The process according to claim 1, wherein the at least one zeolite containing Ti is selected from the group consisting of materials of the structure classes MFI, MEL, MWW, BEA or any mixed structures thereof.

3. The process according to claim 1, wherein the bringing of the solid material or the shaped body in contact with deionized water at a temperature between 120° C. and 175° C. for a duration of 12 to 24 hours is performed in a reactor that is used for the synthesis or treatment of the solid material or in a reactor in which the solid material or the shaped body are used as catalysts in a chemical reaction.

4. An integrated process for the production of a solid material containing at least one zeolite, said process, comprising:
- (I) at least partial crystallization of the solid material containing at least one zeolite which comprises Ti out of a synthesis mixture, resulting in mixture (I) containing the solid material and its mother liquor;
- (II) separating and/or concentrating of the solid material in mixture (I);
- (C) calcining the solid material at temperatures higher than 400° C.;
- (W) bringing the solid material from step (II) in contact with deionized water at a temperature between 120° C. and 175° C. for a duration of 12 to 24 hours;
- (III) agglomerating or granulating or agglomerating and granulating of the solid material from step (W);
wherein step (III) is optional.

5. The integrated process according to claim 4, wherein, after step (W), a repetition of step (II) is performed wherein the solid material is separated from at least parts of the composition containing water.

6. The integrated process according to claim 4, wherein the method of separating and/or concentrating in step (II) is selected from the group consisting of ultrafiltration, spray-drying, spray granulating, and bringing inert support bodies in contact with the synthesis solution from (I).

7. An integrated process for the production of a shaped body, comprising:
- (I) at least partial crystallization of at least one solid material containing at least one zeolite which comprises Ti out of a synthesis mixture, resulting in mixture (I) containing the solid material and its mother liquor;
- (II) separating and/or concentrating of the solid material in mixture (I);
- (C) calcining the solid material at temperatures higher than 400° C.;
- (W) bringing the solid material from step (C) in contact with deionized water at a temperature between 120° C. and 175° C. for a duration of 12 to 24 hours;
- (III) agglomerating or granulating or agglomerating and granulating of the solid material from step (W);
wherein step (III) is optional;
wherein, after step (W) or after step (III), at least one step (S) of shaping the solid material into a shaped body is performed; and
wherein said shaped body comprises the at least one zeolite.

8. The integrated process according to claim 7, wherein the at least one step of shaping the solid material is selected from the group consisting of pelletizing, pressing, extruding, sintering, roasting, briquetting.

9. The integrated process according to 7, wherein the step (W) is performed after the step (S) is performed,
wherein said step (W) either replaces the step (W) performed after step (C) or is performed in addition to the step (W) performed after step (C).

10. The integrated process according to claim 7, wherein after at least one of the steps (W) or (III), a step (C) of calcining the shaped body is performed.

11. A solid material, obtained by an integrated process, comprising:
treating a solid material comprising at least one zeolite which comprises Ti and being at least partly crystalline by bringing said solid material in contact with deionized water at a temperature between 120° C. and 175° C. for a duration of 12 to 24 hours after
at least partial crystallization of the solid material containing the at least one zeolite out of a synthesis mixture, resulting in mixture (I) containing the solid material and its mother liquor; separating the solid material from its mother liquor wherein said separating is a step (II), and calcining the solid material at temperatures higher than 400° C. wherein said calcining is a step (C).

12. The solid material according to claim 11, which displays an increased UV/VIS absorption over materials that have not been brought in contact with deionized water, in the region from 250 to 350 nm.

13. The solid material according to claim 11, which is shaped into a shaped body in a step (S); and
wherein in addition to the step of bringing the solid material in contact with water or instead of said step, the shaped body is brought in contact with water, either directly after the step (S) of shaping the solid material into a shaped body or after a subsequent step (C) of calcining said shaped body, wherein said bringing into contact with water is performed with deionized water at a temperature between 120° C. and 175° C. for a duration of 12 to 24 hours.

14. The solid material according to claim 11, which is shaped into a shaped body in a step (S); and
wherein in addition to the step of bringing the solid material in contact with water or instead of said step, the shaped body is brought. in contact with water, either directly after the step (S) of shaping the solid material into a shaped body or after a subsequent step (C) of calcining said shaped body, wherein said bringing into contact with water is performed with deionized water at a temperature between 120° C. and 175° C. for a duration of 12 to 24 hours.

15. A method of obtaining a reaction product of the reaction of at least one C-C-double bond with at least one hydroperoxide, said method comprising:
reacting at least one compound with at least one C-C-double bond with at least one hydroperoxide in the presence of the solid material according to claim 11.

16. The method of claim 15, wherein said solid material is a catalyst.

17. The method of claim 15, wherein said solid material is a co-catalyst.

* * * * *